US011931181B2

(12) United States Patent
Salzmann et al.

(10) Patent No.: US 11,931,181 B2
(45) Date of Patent: Mar. 19, 2024

(54) SYSTEMS AND METHODS FOR CONFIRMATION OF PRIOR CATHETER TIP PLACEMENT

(71) Applicant: C. R. Bard, Inc., Franklin Lakes, NJ (US)

(72) Inventors: Dennis L. Salzmann, Salt Lake City, UT (US); Eddie K. Burnside, North Salt Lake, UT (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 333 days.

(21) Appl. No.: 17/503,139

(22) Filed: Oct. 15, 2021

(65) Prior Publication Data

US 2022/0031249 A1 Feb. 3, 2022

Related U.S. Application Data

(62) Division of application No. 16/394,897, filed on Apr. 25, 2019, now Pat. No. 11,147,514, which is a
(Continued)

(51) Int. Cl.
*A61B 5/00* (2006.01)
*A61B 1/00* (2006.01)
(Continued)

(52) U.S. Cl.
CPC ........ *A61B 5/6852* (2013.01); *A61B 1/00018* (2013.01); *A61B 5/062* (2013.01);
(Continued)

(58) Field of Classification Search
CPC ...... A61B 2562/0209; A61B 2562/125; A61B 5/062; A61B 8/0841; A61B 5/283; A61M 2025/1056
See application file for complete search history.

(56) References Cited

U.S. PATENT DOCUMENTS 6,006,123 A 12/1999 Nguyen et al.
6,569,101 B2 5/2003 Quistgaard et al.
(Continued)

FOREIGN PATENT DOCUMENTS

WO 2010/022370 A1 2/2010
WO 2011019760 A2 2/2011
(Continued)

OTHER PUBLICATIONS

Benzadon, M. N. et al: "Comparison of the Amplitude of the P-Wave from Intracardiac Electrocardiogram Obtained by Means of a Central Venous Catheter Filled With Saline Solution to That Obtained Via Esophageal Electrocardiogram", American Journal of Cardiology, Cahners Publishing Co., Newton, MA, US, vol. 98, No. 7, Oct. 1, 2006 (Oct. 1, 2006), pp. 978-981.
(Continued)

*Primary Examiner* — Deanna K Hall
(74) *Attorney, Agent, or Firm* — Rutan & Tucker LLP

(57) ABSTRACT

A catheter assembly including one or more conductive pathways to assist with placement of the catheter assembly into a patient's vasculature by enabling ECG signals emanating from the patient's heart to be detected, and a method for reconfirming an initial position of a distal end of a catheter tube of the catheter assembly. The conductive pathways can be configured to reconfirm via ECG signal detection proper placement of the catheter tube at a time subsequent to initial catheter placement into the vasculature. The catheter assembly can include an outer conductive pathway deposited on an outer surface of the catheter tube. The outer conductive pathway can have a distal end located distal to a portion of the catheter tube at a skin insertion site when the catheter tube is inserted into a patient.

16 Claims, 8 Drawing Sheets

Related U.S. Application Data division of application No. 15/177,636, filed on Jun. 9, 2016, now Pat. No. 10,271,795.

(60) Provisional application No. 62/175,115, filed on Jun. 12, 2015.

(51) Int. Cl.
*A61B 5/06* (2006.01)
*A61B 5/283* (2021.01)
*A61B 5/339* (2021.01)
*A61B 8/08* (2006.01)

(52) U.S. Cl.
CPC .............. *A61B 5/283* (2021.01); *A61B 5/339* (2021.01); *A61B 8/0841* (2013.01); *A61B 2562/0209* (2013.01); *A61B 2562/125* (2013.01)

(56) References Cited

U.S. PATENT DOCUMENTS

| | | |
|---|---|---|
| 6,962,566 B2 | 11/2005 | Quistgaard et al. |
| 7,096,059 B2 | 8/2006 | Geddes et al. |
| 7,189,208 B1 | 3/2007 | Beatty et al. |
| 7,270,662 B2 | 9/2007 | Visram et al. |
| 7,349,732 B1 | 3/2008 | Kil et al. |
| 7,479,141 B2 | 1/2009 | Kleen et al. |
| 8,204,582 B2 | 6/2012 | Zantos et al. |
| 9,339,206 B2 | 5/2016 | Grunwald |
| 10,271,795 B2 | 4/2019 | Salzmann |
| 2002/0123679 A1 | 9/2002 | Dominguez |
| 2005/0043640 A1 | 2/2005 | Chang |
| 2005/0197674 A1 | 9/2005 | McCabe et al. |
| 2007/0010753 A1 | 1/2007 | MacAdam |
| 2007/0255270 A1 | 11/2007 | Carney |
| 2008/0125772 A1 | 5/2008 | Stone et al. |
| 2008/0288038 A1 | 11/2008 | Paul et al. |
| 2009/0234328 A1 | 9/2009 | Cox et al. |
| 2010/0004547 A1 | 1/2010 | Scholz et al. |
| 2010/0222664 A1 | 9/2010 | Lemon et al. |
| 2010/0318026 A1 | 12/2010 | Grunwald |
| 2012/0046562 A1 | 2/2012 | Powers et al. |
| 2013/0018248 A1 | 1/2013 | Hurezan |
| 2014/0249505 A1 | 9/2014 | Bukhman |
| 2014/0276620 A1 | 9/2014 | Millett et al. |
| 2015/0080716 A1 | 3/2015 | Powers et al. |
| 2016/0360989 A1 | 12/2016 | Salzmann et al. |
| 2016/0374589 A1 | 12/2016 | Misener et al. |
| 2017/0000367 A1 | 1/2017 | Grunwald |
| 2019/0246983 A1 | 8/2019 | Salzmann et al. |

FOREIGN PATENT DOCUMENTS

| | | |
|---|---|---|
| WO | 2012024577 A2 | 2/2012 |
| WO | 2016/210325 A1 | 12/2016 |

OTHER PUBLICATIONS

Borgobello, Bridget, App allows users to view electrocardiograms on smartphones dated Oct. 15, 2010; printed from http://www.gizmag.com/app-to-view-electrocardiograms-on-smartphones/16664/ on Feb. 4, 2011.

Cavatorta, et al., "Central Venous Catheter Placement in Hemodialysis: Evaluation of Electrocardiography Using a Guidewire." The Journal of Vascular Access, vol. 2, pp. 45-50, 2001.

Cheng, Ki et al, A Novel Approach of Intravenous Electrocardiograph Technique in Correct Position the Long-Term Central Venous Catheter, Kaohsiung J Med Sci, pp. 241-247, vol. 16 No 5, May 2000 (Abstract only).

Chu, et al., "Accurate Central Venous Port-A Catheter Placement: Intravenous Electrocardiography and Surface Landmark Techniques Compared by Using Transesophageal Echocardiography." The International Anesthesia Research Society, vol. 98, pp. 910-914, 2004.

Felleiter P et al, Use of Electrocardiographic Placement Control of Central Venous Catheters in Austria, Acta Med Austriaca, pp. 109-113, vol. 26 No 3, 1999 (Abstract only).

Gebhard, et al., "The accuracy of Electrocardiogram-Controlled Central Line Placement." The International Anesthesia Research Society, vol. 104, No. 1 Jan. 1, 2007.

Madan, et al. "Right Atrial Electrocardiography: A Technique for the Placement of Central Venous Catheters for Chemotherapy or Intravenous Nutrition." British Journal of Surgery, vol. B1, pp. 1604-1605, 1994.

McDonnall, "Intra-Atrial Electrocardiography (ECG) for Catheter Placement." Literature review prepared for Bard Access Systems, Oct. 2007.

Moureau, Nancy L. et al., "Electrocardiogram (EKG) Guided Peripherally Inserted Central Catheter Placement and Tip Position: Results of a Trial to Replace Radiological Confirmation," Journal of the Association for Vascular Access, pp. 8-14, vol. 15, No. 1, 2010.

Murthy, Vrudhula et al., Analysis of Power Spectral Densities of Electrocardiograms, Mathematical Biosciences, pp. 41-51, vol. 12 No 1-2, Oct. 1971.

Pawlik, et al., "Central Venous Catheter Placement: Comparison of the Intravascular Guidewire and the Fluid Column Electrocardiograms." European Journal of Anaesthesiology, vol. 41, pp. 594-599, 2004.

Pittiruti, et al. "The electrocardiographic method for positioning the tip of central venous catheters" JAVA, pp. 1-12, Feb. 12, 2011.

Simon, et al., "Central Venous Catheter Placement in Children: Evaluation of Electrocardiography Using J-Wire." Paediatric Anaesthesia vol. 9, pp. 501-504, 1999.

Smith, Brigham, et al., Intravenous electrocardiographic guidance for placement of peripherally inserted central catheters, Journal of Electrocardiology 43 (2010) 274-278.

Stas, M et al, Peroperative Intravasal Electrographic Control of Catheter Tip Position in Access Ports Placed by Venous Cut-Down Technique, EJSO, pp. 316-320, vol. 27, 2001.

U.S. Appl. No. 15/177,636, filed Jun. 9, 2016 Non-Final Office Action dated Jul. 27, 2018.

U.S. Appl. No. 15/177,636, filed Jun. 9, 2016 Restriction Requirement dated Apr. 20, 2018.

U.S. Appl. No. 16/394,897, filed Apr. 25, 2019 Non-Final Office Action dated Mar. 16, 2021.

U.S. Appl. No. 16/394,897, filed Apr. 25, 2019 Notice of Allowance dated Jul. 13, 2021.

U.S. Appl. No. 16/394,897, filed Apr. 25, 2019 Restriction Requirement dated Jan. 11, 2021.

Watters, et al. "Use of Electrocardiogram to Position Right Atrial Catheters During Surgery." Annals of Surgery, vol. 225, No. 2, pp. 165-171, 1997.

Wilson, R. G. et al, Right Atrial Electrocardiography in Placement of Central Venous Catheters, The Lancet, pp. 462-463, Feb. 27, 1988.

Yoshida, Teruhisa et al, Detection of Concealed Left Sided Accessory Atrioventricular Pathway by P Wave Signal Averaged Electrocardiogram, J Am Coll Cardiol, pp. 55-62, 1999.

SYSTEMS AND METHODS FOR CONFIRMATION OF PRIOR CATHETER TIP PLACEMENT

PRIORITY

This application is a division of U.S. patent application Ser. No. 16/394,897, filed Apr. 25, 2019, now U.S. Pat. No. 11,147,514, which is a division of U.S. patent application Ser. No. 15/177,636, filed Jun. 9, 2016, now U.S. Pat. No. 10,271,795, which claims the benefit of U.S. Provisional Application No. 62/175,115, filed Jun. 12, 2015, each of which is incorporated herein by reference in its entirety.

BRIEF SUMMARY

Briefly summarized, embodiments of the present invention are directed to a catheter assembly including one or more conductive pathways is disclosed. The conductive pathways are configured to assist with initial placement of the catheter assembly into the vasculature or other suitable location of the patient by enabling ECG signals emanating from the heart of the patient to be detected. In addition, the conductive pathways are configured to be used to confirm via ECG signal detection proper placement of the catheter assembly at a time subsequent to the initial placement of the catheter assembly into the patient vasculature.

In one embodiment, therefore, a catheter assembly is disclosed, comprising an elongate catheter tube defining at least one lumen, a first conductive pathway extending distally from a proximal point on the catheter assembly to a predetermined distal location on the catheter tube, and a second conductive pathway at least partially disposed on an outer surface of the catheter tube and extending distally from a proximal point of the catheter assembly to a predetermined distal location on the catheter tube. The predetermined distal location of the second conductive pathway is configured to be located distal to a portion of the catheter tube that is adjacent a skin insertion site of the catheter tube when the catheter assembly is inserted into a patient.

These and other features of embodiments of the present invention will become more fully apparent from the following description and appended claims, or may be learned by the practice of embodiments of the invention as set forth hereinafter.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Reference will now be made to figures wherein like structures will be provided with like reference designations. It is understood that the drawings are diagrammatic and schematic representations of exemplary embodiments of the present invention, and are neither limiting nor necessarily drawn to scale.

For clarity it is to be understood that the word "proximal" refers to a direction relatively closer to a clinician using the device to be described herein, while the word "distal" refers to a direction relatively further from the clinician. For example, the end of a catheter placed within the body of a patient is considered a distal end of the catheter, while the catheter end remaining outside the body is a proximal end of the catheter. Also, the words "including," "has," and "having," as used herein, including the claims, shall have the same meaning as the word "comprising."

Embodiments of the present invention are generally directed to a catheter assembly for placement within the vasculature or other internal portion of a body of a patient to provide access thereto. A peripherally inserted central catheter ("PICC") is one example of such a catheter, though other types of catheters are also contemplated. The catheter assembly includes one or more electrically conductive pathways. The conductive pathways are configured to assist with initial placement of the catheter assembly into the vasculature or other suitable location of the patient by enabling ECG signals emanating from the heart of the patient to be detected. The detected ECG signals are used by a clinician to determine when the distal end of the catheter has been positioned proximate an ECG signal-emitting node of the patient's heart, such as the SA node, in one embodiment.

In addition, the conductive pathways of the catheter assembly are configured to be used at a time subsequent to the initial placement of the catheter assembly into the patient vasculature so as to confirm that the distal end of the catheter has not undesirably moved substantially from its initially placed position. Such confirmation of catheter distal tip position is desired so as to ensure that medicaments/fluids infused through the catheter assembly are delivered to the desired location within the patient body. Also, such reconfirmation of catheter distal end position helps in preventing a health risk to the patient that may be caused by undesired catheter repositioning.

Figure 1:
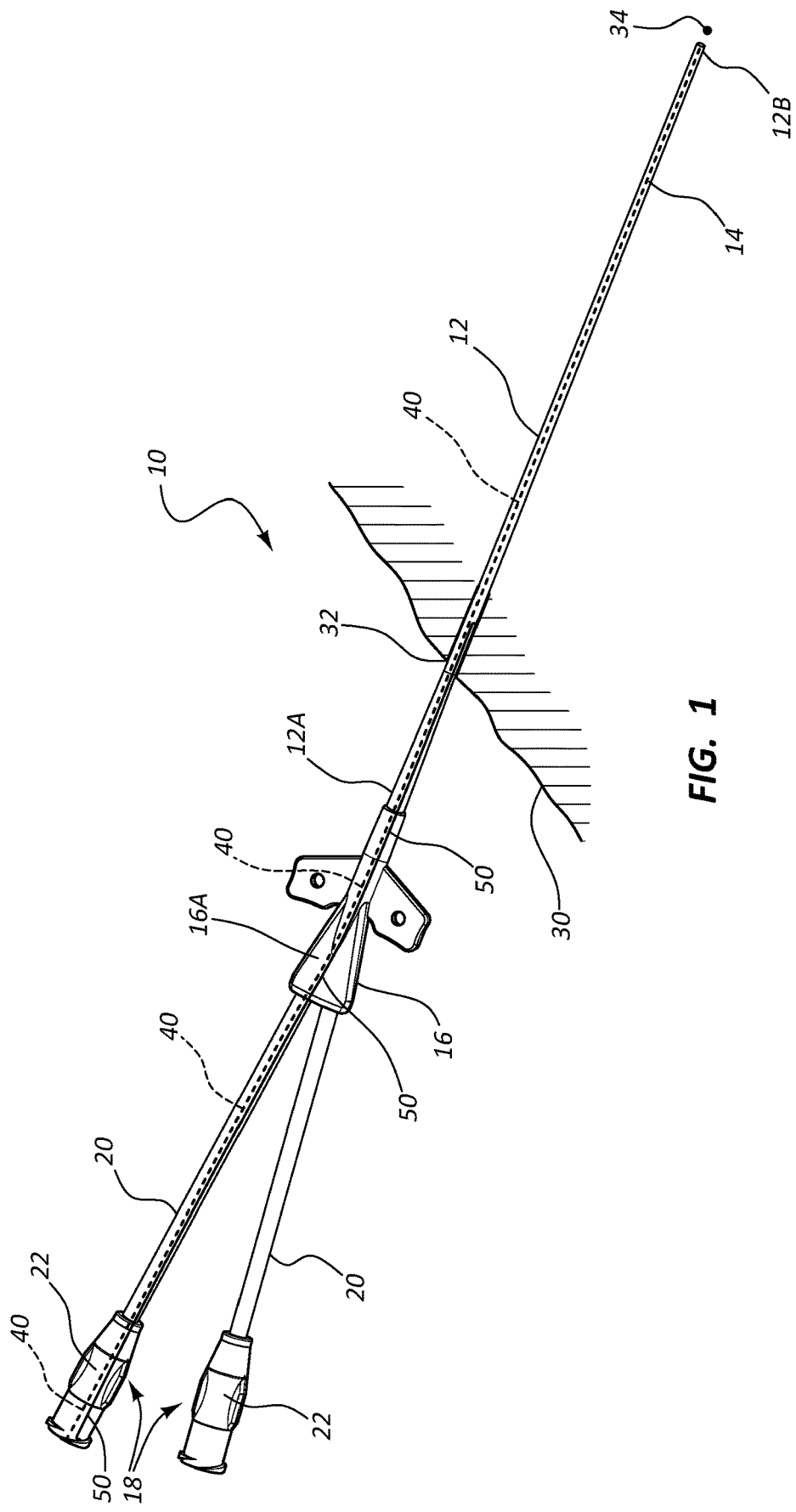
FIG. 1 is a perspective view of a catheter assembly in accordance with one embodiment.

Reference is first made to FIG. 1, which depicts various details of a catheter assembly ("catheter"), generally depicted at 10, in accordance with one embodiment. As shown, the catheter 10 includes an elongate catheter tube 12 that defines one or more lumens 14 extending between an open proximal end 12A and an open distal end 12B of the catheter tube. In the illustrated embodiment, for instance, the catheter tube 12 defines two lumens, though one, three, four, or other numbers of lumens are possible. Also, though shown configured as a PICC, the catheter 10 is representative of a variety of catheters and elongate tubular medical devices that can benefit from the present disclosure, including but not limited to central venous catheters, acute and chronic dialysis catheters, peripheral IVs, Foley and urinary catheters, arterial catheters, feeding tubes, balloon catheters, etc. Thus, the discussion to follow is not intended to be limited to the illustrated embodiments.

The lumens 14 at the proximal end 12A of the catheter tube 12 are in fluid communication with corresponding hollow fluid passages 16A defined through a bifurcation hub 16. In turn, proximal ends of the fluid passages 16A are in fluid communication with corresponding hollow extension tubes 20 of extension legs 18. Each extension leg 18 includes a connector 22 for enabling connection of the catheter 10 to fluid infusion/aspiration devices, including syringes, etc. Note that the particular details of the catheter can vary from what is shown and described herein.

FIG. 1 shows in simplified form the catheter 10 inserted through an insertion site 32 defined through skin 30 of the patient. In the present embodiment, the portion of the catheter tube 12 that is inserted within the patient is disposed in a vein or other portion of the vasculature of the patient such that the distal end 12B of the catheter tube is disposed proximate a desired location 34. In one embodiment, the desired location 34 includes the lower $\frac{1}{3}^{rd}$ portion of the superior vena cava ("SVC") near the heart of the patient. Of course, other destinations for the desired location are possible.

FIG. 1 further shows that the catheter 10 includes a first conductive pathway 40. As shown, the first conductive pathway 40 substantially extends from a proximal end of the catheter 10 to a distal end thereof and includes a strip (or other form) of conductive material so as to permit the passage of electrical signals therethrough. In the present embodiment, the first conductive pathway 40 includes an elongate strip of metal, such as copper, aluminum, etc., or other electrically conductive material continuously disposed on an inner wall surface of one of the lumens 14 of the catheter tube, on an inner wall surface of one of the passages 16A of the bifurcation hub 16, and on an inner wall surfaces of the corresponding extension tube 20 and connector 22, as shown. So disposed, the conductive pathway 40 extends from a proximal end of the catheter 10 to a distal end thereof, thus forming an electrically conductive path that runs the entire length of the catheter, though in other embodiments it is appreciated that that the length of the conductive pathway can vary from this. In another embodiment, the conductive pathway is defined in the walls of the catheter tube 12, passage 16A, extension tube 20, and connector 22, and thus is not disposed on the inner surfaces of the components but rather buried in the corresponding walls. In addition to this, other modes can be employed to define the conductive pathways described above.

As mentioned, the first conductive pathway 40 disposed as described above establishes an electrical communication path between the distal end 12B of the catheter tube 12 and a proximal end of the catheter 10. This in turn enables intravascular ECG signals emitted by a node of the heart of the patient and carried by the blood in the vein or other vessel in which the catheter 10 is disposed to be detected at the distal tip 12B of the catheter tube and conveyed via the first conductive pathway 40 to a proximal end of the catheter 10, where the signals may be forwarded to and analyzed by a catheter placement system or other ECG monitoring system, such as the catheter placement system 210 shown in FIGS. 7 and 8, described further below. A tether or other suitable connection can be employed to operably connect the proximal end of the first conductive pathway 40 at the connector 22 to the catheter placement system. It is appreciated that, in one embodiment, the first conductive pathway, as well as the other electrical pathways described herein, can terminate at a point distal to the proximal end of the catheter 10, such as at a predetermined point along the length of the extension leg 18 or the bifurcation hub 16, for instance.

In the present embodiment, the distal end of the first conductive pathway 40 is disposed at the open distal end 12B of the catheter tube 12, where it acts as a sensor for detecting ECG signals emitted by one or more nodes of the heart, such as the SA node, for instance. Analysis of the ECG signals detected by the distal end of the first conductive pathway 40 at the distal end 12B of the catheter tube 12 and conveyed to the catheter placement system (such as the system 210 shown in FIGS. 7 and 8, below) via the first conductive pathway 40 enables a user to determine proximity of the catheter tube distal end to the ECG signal-emitting SA node (or other suitable heart node) in order to place the catheter tube distal end at the desired location 34, which in the present embodiment corresponds to the lower $\frac{1}{3}^{rd}$ of the superior vena cava ("SVC"), an oft-desired desired location for a PICC. As such, the first conductive pathway 40 assists a user in determining when the distal end 12B of the catheter tube has arrived at the desired location 34, in the present embodiment. In addition to the description and operation of the catheter placement system 210 of FIGS. 7 and 8. Further details regarding the catheter placement system and the use of ECG signals to locate a catheter within the vasculature of a patient can be found in U.S. Pat. No. 9,636,031, filed Sep. 29, 2010, and titled "Stylets for Use with Apparatus for Intravascular Placement of a Catheter," which is incorporated herein by reference in its entirety.

FIG. 1 shows that the catheter 10 further includes a second conductive pathway 50. As shown, the second conductive pathway 50 substantially extends from a proximal end of the catheter 10 to an intermediate point along the catheter tube 12 that corresponds to the portion of the catheter tube that is disposed proximate the insertion site 32 when the catheter tube is transcutaneously inserted through the skin 30 of the patient body. As with the first conductive pathway 40, the second conductive pathway 50 includes a strip (or other form) electrically conductive material so as to permit the passage of electrical signals via the pathway. In the present embodiment, the second conductive pathway 50 includes an elongate strip of metal, such as copper, aluminum, etc., or other electrically conductive material continuously disposed continuously disposed on an outer surface of catheter tube 12, an outer surface of the bifurcation hub 16, and an outer surface of the corresponding extension tube 20 and connector 22. Note that the first and second conductive pathways 40, 50 are electrically isolated from one another in the catheter 10. Note that in one embodiment the conductive material of the first and/or second conductive pathways 40, 50 includes a conductive ink, including silver-based and carbon-black inks, though a variety of other materials can be employed. In another embodiment, at least a portion of the second conductive pathway 50 is defined in the walls of the catheter tube 12, passage 16A, extension tube 20, and connector 22 instead of on an outer surface of these components. In such a case, only a distal portion of the of the second conductive pathway 50 need be externally exposed on the catheter tube 12 so as to be able to function, as will be described further below.

The second conductive pathway 50 provides an electrically conductive pathway between the proximal end of the catheter 10 and a point proximate the skin surface 30 of the patient near the insertion site 32. In detail, a portion of the second conductive pathway 50 is disposed in intimate contact with the skin 30 about the insertion site 32 when the catheter 10 is transcutaneously inserted therethrough and positioned for use. Due to the disposal of at least its distal portion on the outer surface of the catheter tube 12, the second conductive pathway 50 is able to detect skin-based, reference ECG signals present at/near the surface of the skin 30, which emanate from the SA node of the patient heart (or other suitable node). The second conductive pathway 50 provides a pathway for the conveyance of the detected reference ECG signals to the catheter placement system, such as the catheter placement system 210 shown in FIGS. 7 and 8, for instance. These reference ECG signals can be employed by the catheter placement system 10 (or other suitable ECG monitoring system), together with the detected intravascular ECG signal described above, in the present embodiment, to assist in placing the distal end 12B of the catheter tube 12 at the desired location 34, such as the lower $\frac{1}{3}^{rd}$ portion of the SVC, as mentioned. A tether or other suitable connection can be employed to operably connect the proximal end (or other terminus) of the second conductive pathway 50 at the connector 22 to the catheter placement system.

Figure 2:
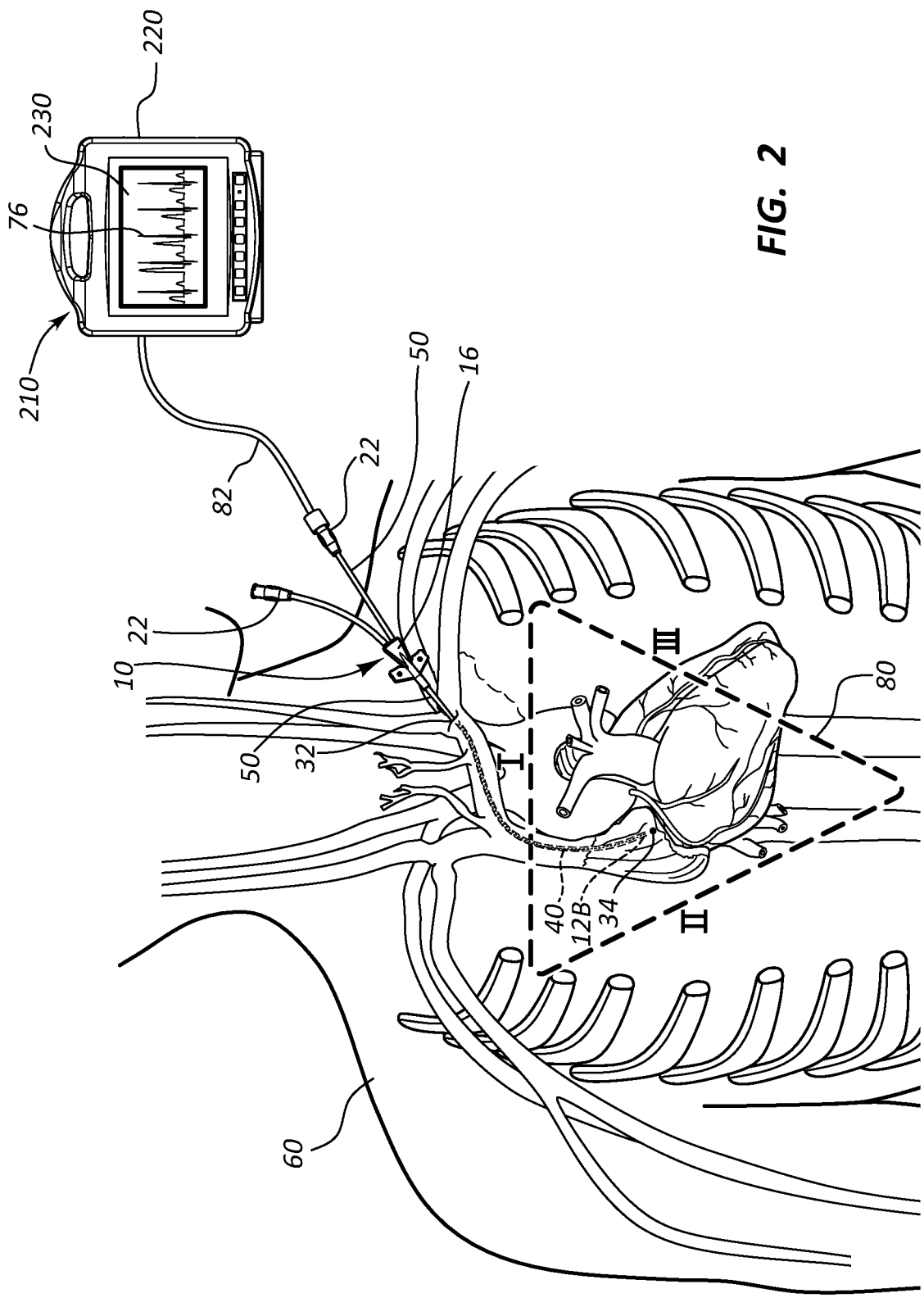
FIG. 2 is a simplified view of a patient with the catheter assembly of FIG. 1 inserted therein.

In view of the above, and as depicted in FIG. 2—which shows the catheter assembly 10 inserted into a vein of a patient during a procedure to position the catheter assembly in preparation for use—the intravascular ECG signals emanating from the SA node of the heart are detected by the distal portion of the first conductive pathway 40, disposed at the distal end 12B of the catheter tube 12. Correspondingly, the reference ECG signals emanating from the SA node are detected by the second conductive pathway 50 at the surface of the skin 30 proximate the insertion site 32. The intravascular and reference ECG signals can be used by the catheter placement system 210 (FIGS. 7 and 8) to assist with placement of the catheter assembly 10 into the vasculature of the patient 60 such that the distal end 12B of the catheter tube 12 is disposed proximate the desired location 34, as discussed and as shown in FIG. 2.

FIG. 2 further shows one example of attachment of the first and second conductive pathways 40, 50 to the catheter placement system 10, wherein a tether 82 attaches to the corresponding connector 22 of the catheter assembly 10 so as to operably connect with proximal terminations of the first and second conductive pathways. The opposite end of the tether 82 attaches to a console 220 (containing a processor and various system components as discussed further below) of the catheter placement system 210 so as to enable intravascular and reference ECG signals detected by the first and second conductive pathways 40 and 50, respectively, to be received and used by the catheter placement system. Other connective schemes can be employed, in other embodiments. FIG. 2 additionally shows a display 230 of the catheter placement system console 220 and an ECG waveform 76 as one example depiction of an intravascular ECG signal as detected and displayed by the catheter placement system 210.

FIG. 2 further shows that, in the case of a left-sided placement of the catheter 10 into the patient 60, the vascular path taken by the catheter tube 12 after insertion into the patient via the insertion site 32 enables the first and second conductive pathways 40 and 50 to cooperate (as intravascular and reference ECG signals, respectively) in establishing a lead I configuration, according to Einthoven's triangle of electrocardiography 80. For catheter insertions into the right side of the torso of the patient 60, a lead II configuration would be established, though it is appreciated that other lead configurations could also be established, as appreciated by one skilled in the art.

As mentioned above, the intravascular and reference ECG signals respectively detected by the first and second conductive pathways 40 and 50 can be received and processed as needed by the catheter placement system 210, including depiction of the display 230, as shown in FIG. 2, to assist the user of the catheter placement system in determining when the distal end 12B of the catheter tube 12 has arrived at the desired location 34. Also and in accordance with the present embodiment, the depicted catheter 10 and catheter placement system 210 can be employed to confirm that the distal end 12B of the catheter tube 12 has not moved away from the desired location 34 at a later time after initial placement of the catheter into the patient. In the present embodiment, this reconfirmation of catheter tube distal end placement at the desired location 34 is accomplished by measuring the ECG signals conveyed by the first and second conductive pathways 40 and 50 at the later time after initial catheter placement and comparing the resultant ECG waveform (such as the waveform 76 on the display 230 shown in FIG. 2) as received and processed by the catheter placement system 210. If the ECG waveform at the later time matches that measured at the time of initial catheter placement, then no movement of the distal end 12B of the catheter tube 12 has occurred; differing ECG waveforms, however, may indicate subsequent movement of the catheter tube distal end. In addition to the ECG waveform 76, which in the present embodiment can include data from either or both of the intravascular and reference ECG signals, other data indicative of the final position of the distal end 12B of the catheter tube within the vasculature (or other location) of the patient 60 can be detected, used, and/or stored by the clinician and/or catheter placement system 210 at the time of initial placement of the catheter 10 into the patient. Indeed, it is appreciated that the clinician and/or the catheter placement system 210 preserves a record of the ECG waveform 76 or other data indicative of catheter tube distal end position at the time of initial placement of the catheter 10 into the patient 60 so that comparison of data indicative of catheter tube distal end position at the later time after initial placement can be made so as to determine whether undesired catheter tube distal end movement has occurred.

In one embodiment, the first and second conductive pathways 40 and 50 are deposited on their respective catheter tube surfaces via deposition or painting processes using metal, conductive ink, or other suitable material. In another embodiment, the first and second conductive pathways 40 and 50 are insert-molded or otherwise molded or extruded with the catheter tube during its manufacture. These and other manufacturing schemes are therefore contemplated.

Figure 3:
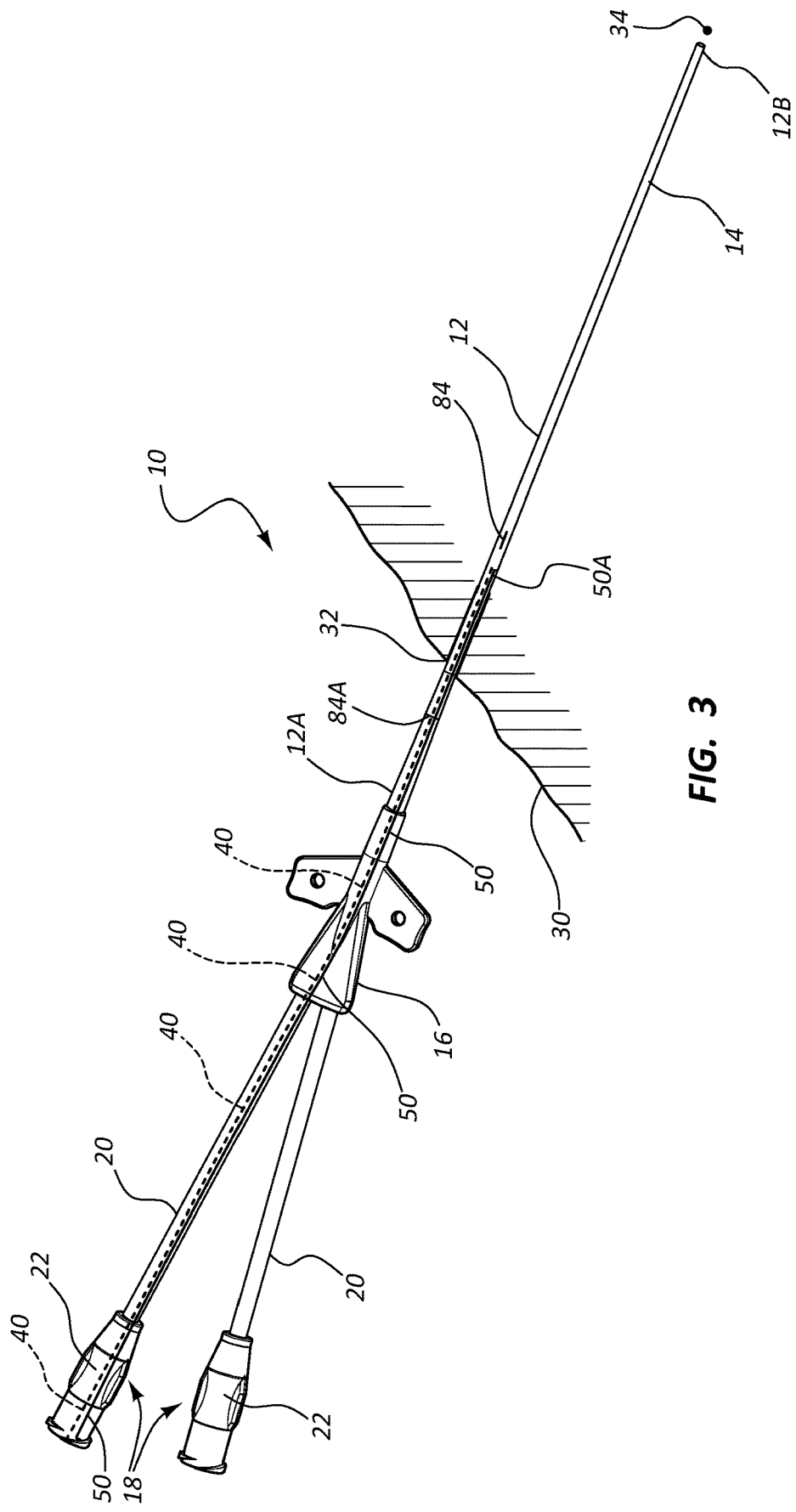
FIG. 3 is a perspective view of a catheter assembly in accordance with one embodiment.

FIG. 3 shows the catheter 10 according to another embodiment, wherein the first conductive pathway 40 disposed on an inner surface of the lumen 14 of the catheter tube 12 does not extend to the distal end 12B of the catheter tube, but rather terminates proximal thereto. Correspondingly, the lumen 14 is removably filled with a conductive solution 84, such as saline or other suitable conductive solution, of sufficient quantity so as to extend proximally from the distal end 12B to a solution level 84A that is proximally past a distal termination point 40A of the first conductive pathway 40. So disposed, the conductive solution 84 provides a conductive path from the distal end 12B of the catheter tube 12 to the distal termination point 40A of the first conductive pathway 40, which pathway can then convey detected ECG signals to the proximal end of the catheter 10. Thus, intravascular ECG signals present in the blood of the vein or vessel in which the catheter tube 12 is disposed are conveyed proximally from the blood into the conductive solution 84 present in the catheter tube lumen 14 to the first conductive pathway 40 and proximally to the corresponding catheter connector 22 in the present embodiment, then on (via the tether 82 (FIG. 2) to the catheter placement system 210 (or other suitable destination), as described above. The particular distal termination point 40A for the first conductive pathway 40 can vary from what is shown and described herein.

Figure 6:
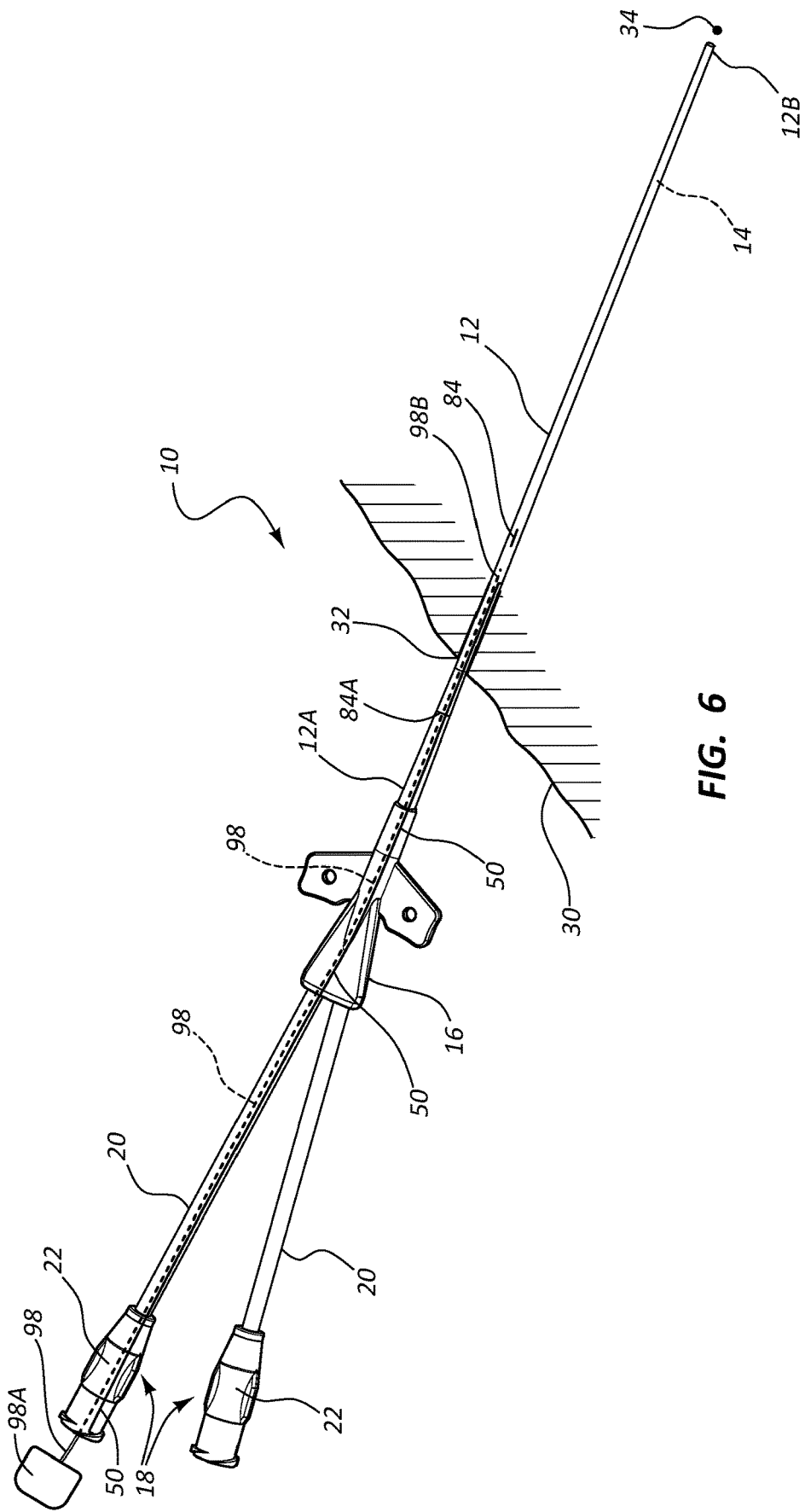
FIG. 6 is a perspective view of an inserted catheter assembly in accordance with one embodiment.

FIG. 6 shows that, in another embodiment, the first conductive pathway 50 can include other elements, such as an elongate conductive stylet 98 that is removably received within the lumen 14, to convey ECG signals through the catheter 10. The stylet 98 can be used in conjunction with other elements, such as in FIG. 6 wherein the conductive solution 84 is infused into the distal portion of the catheter tube lumen 14 so as to define the solution level 84A. The stylet 98 is disposed in the proximal portion of the catheter tube lumen 14 with a distal end 98B of the stylet extending distally past the solution level 84A so as to be in fluid communication with the conductive solution 84 and to provide a conductive path through the catheter 10. In another embodiment, the stylet 98 can extend substantially the entire length of the catheter 10. These and other modifications are therefore contemplated.

Figure 4:
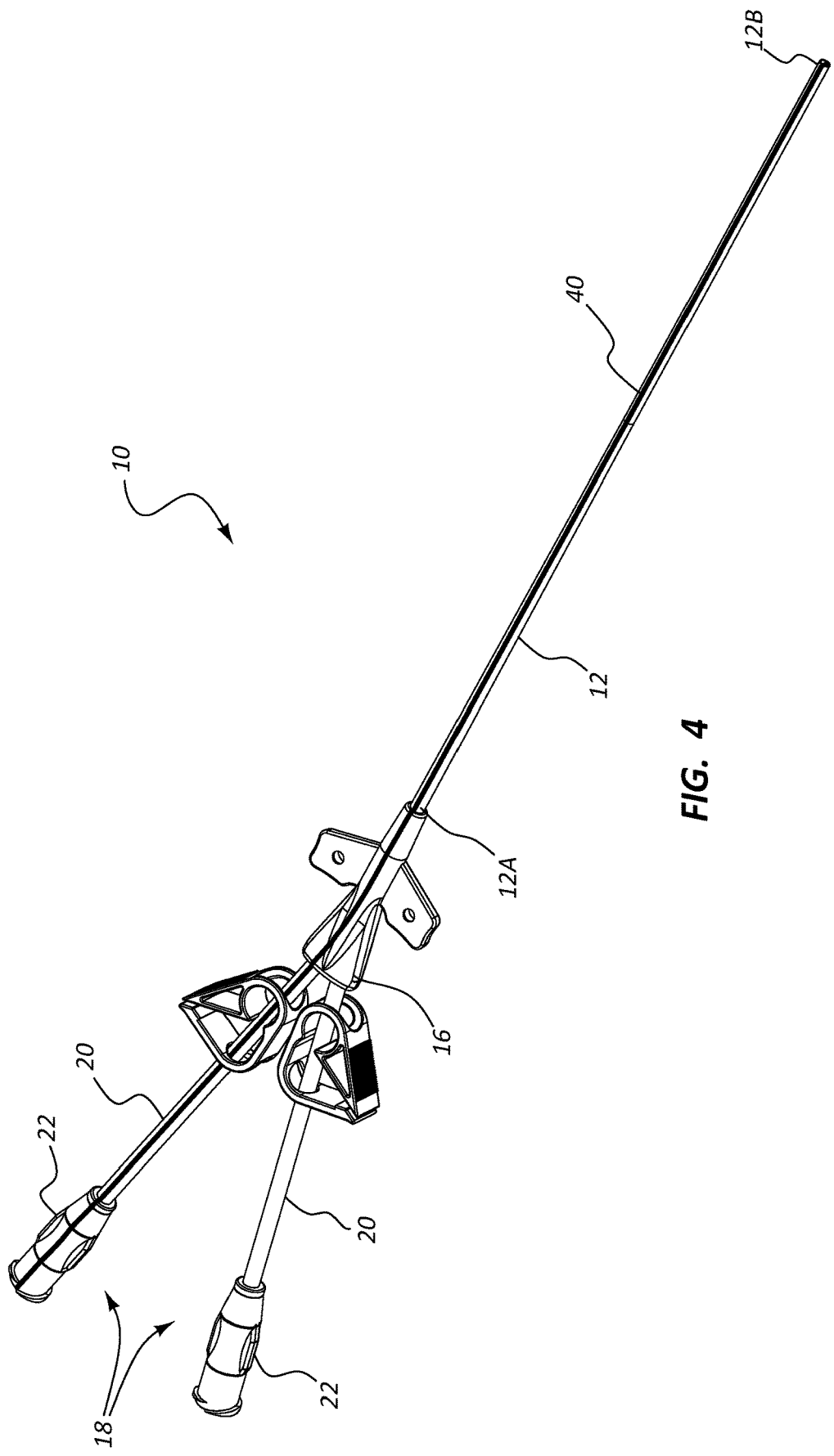
FIG. 4 is a perspective view of a catheter assembly in accordance with one embodiment.

FIG. 4 shows the catheter 10 according to another embodiment, wherein the first conductive pathway 40 is disposed on an outer surface of the catheter tube 12, corresponding extension tube 20, and corresponding connector 22 so as to extend the longitudinal length of the catheter, with no second conductive pathway included. In another embodiment, the second conductive pathway could be included on another portion of the outer surface of the catheter 10. It is therefore appreciated that the location and placement of the first and second conductive pathways can vary from what is shown and described herein.

Figure 5:
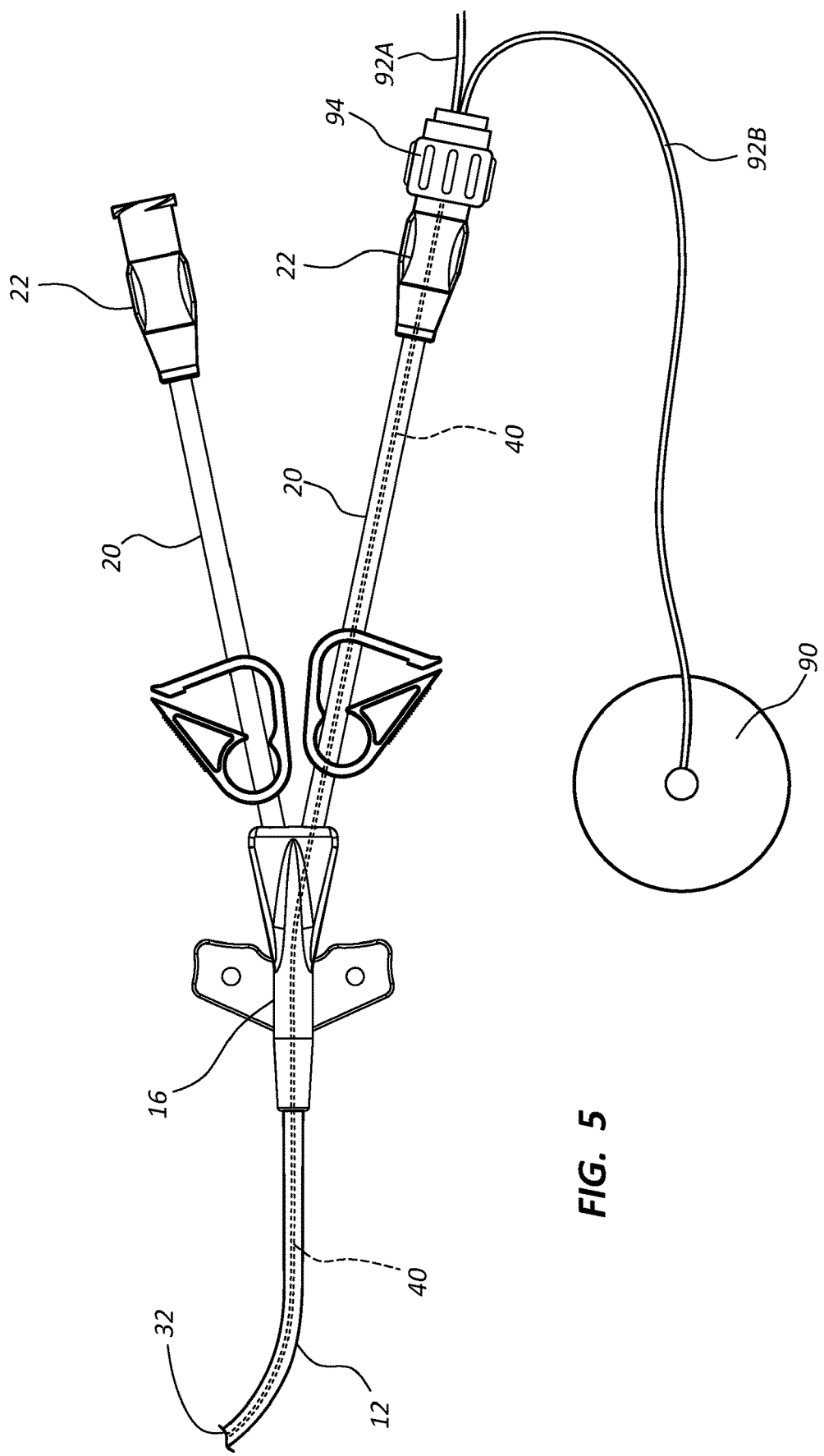
FIG. 5 is a perspective view of an inserted catheter assembly in accordance with one embodiment.

FIG. 5 shows the catheter 10 according to another embodiment, wherein the catheter tube 12 is partially inserted into the patient via the insertion site 32. The first conductive pathway 40 is shown extending through an inner path of the catheter 10, as in the embodiment shown in FIG. 1. A connector interface 94 is shown operably attached to the connector 22 through which the first conductive pathway 40 extends. The connector interface 94 includes a tether 92A for operably connecting to the catheter placement system 210 (FIGS. 7, 8) or other suitable ECG monitoring device so as to provide an intravascular ECG signal.

An ECG electrode 90 is also shown disposed on the skin of the patient and operably connected to a tether 92B so as to provide a skin reference ECG signal to the catheter placement device 210 via the tether 92A, or by other suitable mode. The ECG electrode 90 in the present embodiment thus provides another example of a conductive pathway, in addition to the second conductive pathway 50 (FIG. 1), for providing a reference ECG signal to the catheter placement device 210 or other suitable ECG monitoring device.

Figure 7:
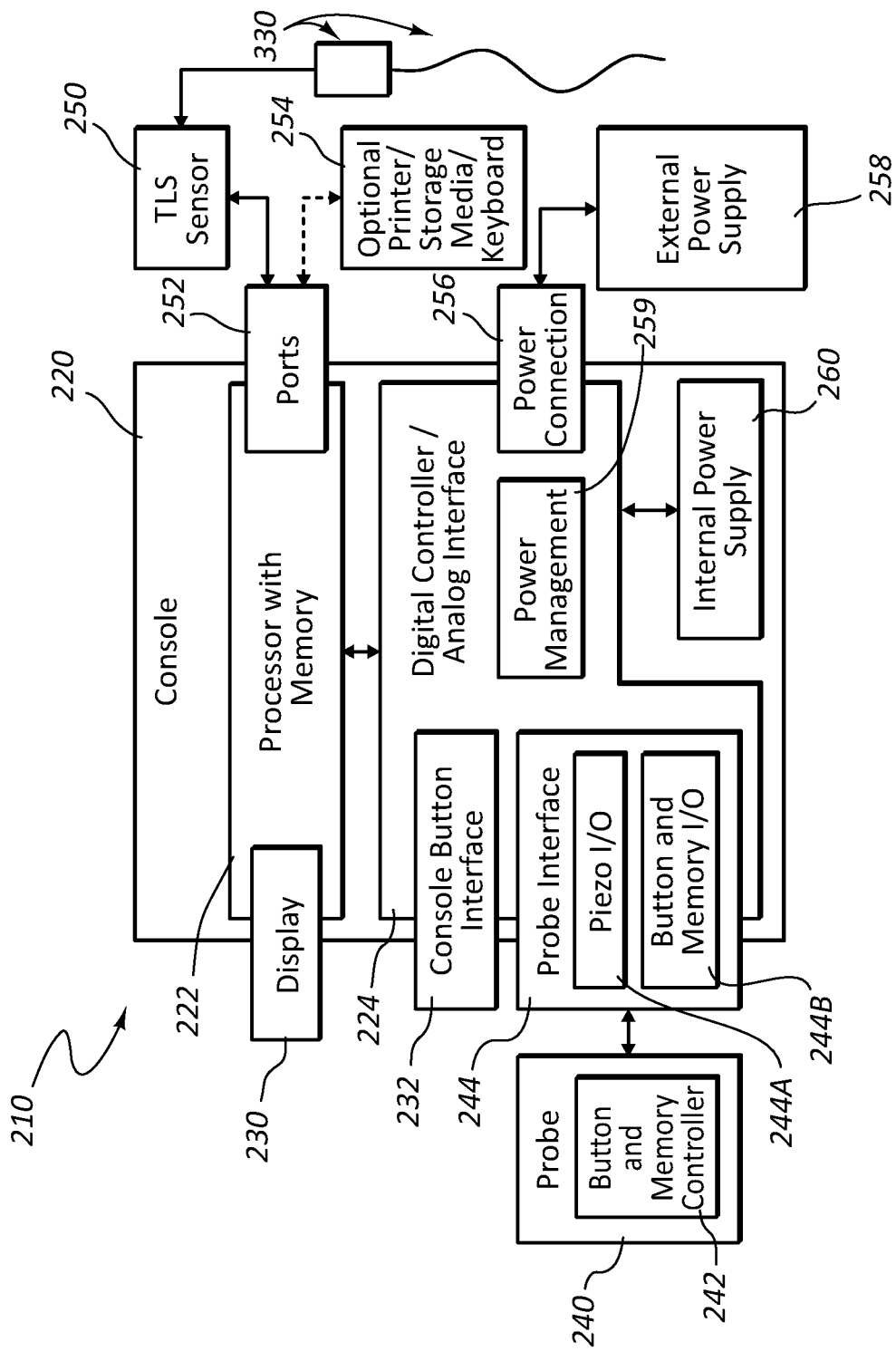
FIG. 7 is a block diagram of a catheter placement system according to one embodiment.
Figure 8:
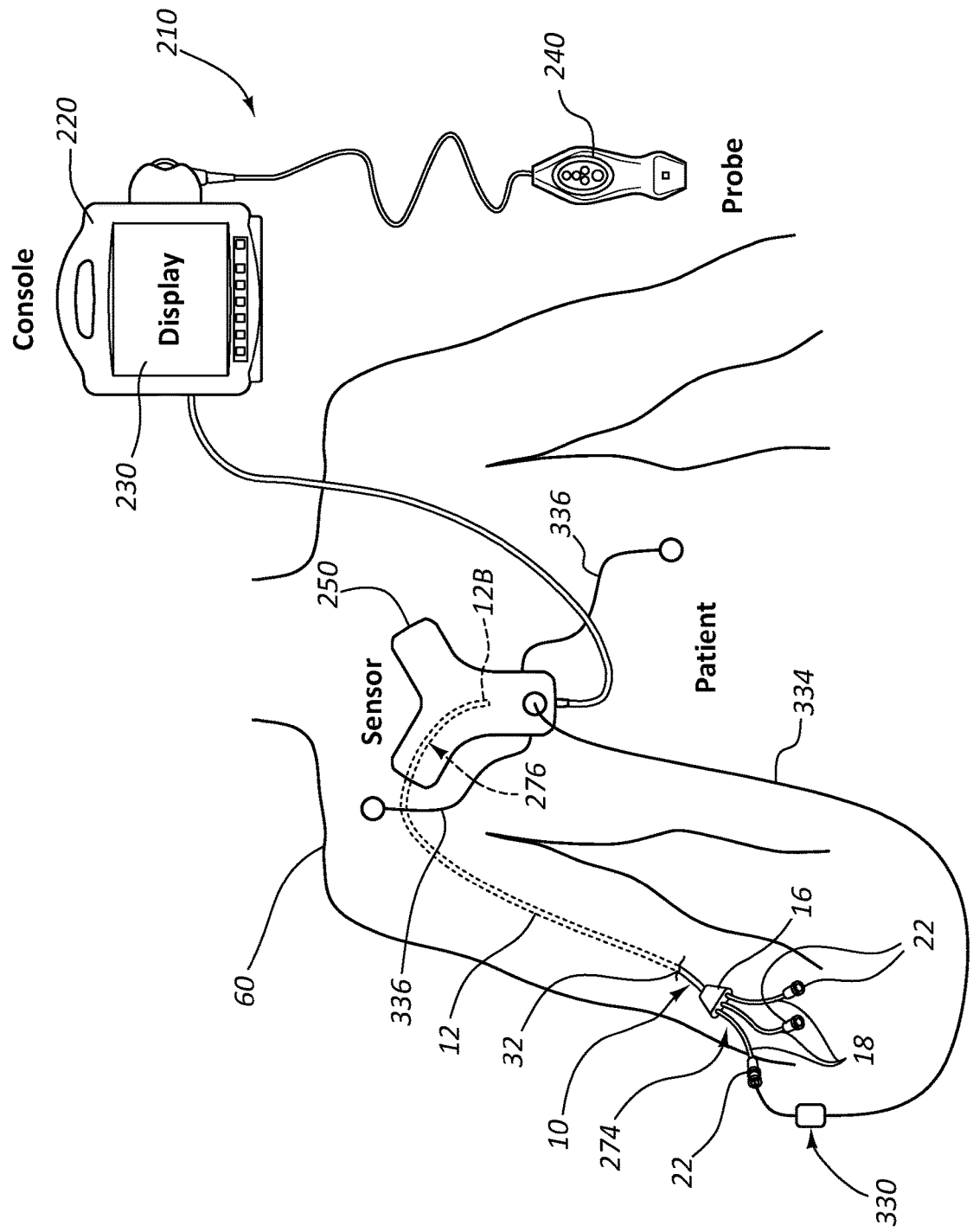
FIG. 8 is a view of the catheter placement system of FIG. 7 together with a catheter assembly inserted into a patient.

FIGS. 7 and 8 depict various details regarding the afore-discussed catheter placement system 210, also referred to herein as a "placement system" or "system," for assisting a clinician in the placement of the catheter 10 or other medical device within the body of a patient, such as within the vasculature. As mentioned, the catheter placement system enables a distal tip of the catheter 10 to be placed within the patient vasculature in desired proximity to the heart using ECG signals produced by the patient's heart. In one embodiment, the desired location is such that the distal tip of the catheter is disposed in the lower $\frac{1}{3}^{rd}$ portion of the superior vena cava ("SVC"). As mentioned, the guidance and placement system analyzes the ECG signals of the patient to determine when the catheter has reached its intended destination within the vasculature, then notifies the clinician via the display 230, for instance. Thus, the system includes an ECG modality for assisting in medical device placement within the patient.

In one embodiment, the above-referenced ECG guidance modality of the guidance and placement system is accompanied by an ultrasound ("US") modality to assist with initial insertion of the medical device into the body, and a magnetic element-based tracking, or tip location system ("TLS") modality to track the position and orientation of the medical device as it advances toward its intended destination. In one embodiment, the magnetic element-based TLS modality employs an electromagnetic assembly.

FIGS. 7 and 8 depict various components of the catheter placement system 210, configured in accordance with one example embodiment. As shown, the system 210 generally includes the console 220, the display 230, a probe 240, and a sensor 250, each of which is described in further detail below.

FIG. 8 shows the general relation of these components to a patient 60 during a procedure to place the catheter 10 into the patient vasculature through a skin insertion site 73. FIG. 2 shows that the catheter 10 generally includes a proximal portion 274 that remains exterior to the patient and a distal potion 276 that resides within the patient vasculature after placement is complete. In the present embodiment, the system 210 is employed to ultimately position a distal tip 12B of the catheter tube 12 in a desired position within the patient vasculature. In one embodiment, the desired position for the catheter tube distal tip 12B is proximate the patient's heart, such as in the lower one-third ($\frac{1}{3}^{rd}$) portion of the SVC. Of course, the system 210 can be employed to place the catheter distal tip in other locations. The catheter proximal portion 274 further includes the bifurcation hub 16 and one or more of the extension legs 18 extending proximally from the hub, as described above.

In further detail, FIG. 7 depicts that a processor 222, including non-volatile memory such as EEPROM for instance, is included in the console 220 for controlling system function during operation of the system 210, thus acting as a control processor. A digital controller/analog interface 224 is also included with the console 220 and is in communication with both the processor 222 and other system components to govern interfacing between the probe 240, sensor 250, and other system components.

The system 210 further includes ports 252 for connection with the sensor 250 and optional components 254 including a printer, storage media, keyboard, etc. The ports in one embodiment are USB ports, though other port types or a combination of port types can be used for this and the other interfaces connections described herein. A power connection 256 is included with the console 220 to enable operable connection to an external power supply 258. An internal battery 260 can also be employed, either with or exclusive of an external power supply. Power management circuitry 59 is included with the digital controller/analog interface 224 of the console to regulate power use and distribution.

The display 230 in the present embodiment is integrated into the console 220 and is used to display information to the clinician during the catheter placement procedure. In another embodiment, the display may be separate from the console. As will be seen, the content depicted by the display 230 changes according to which mode the catheter placement system is in: US, TLS, or in other embodiments, ECG tip confirmation. In one embodiment, a console button interface 232 and buttons included on the probe 240 can be used to immediately call up a desired mode to the display 230 by the clinician to assist in the placement procedure. In one embodiment, information from multiple modes, such as TLS and ECG, may be displayed simultaneously. Thus, the single display 230 of the system console 220 can be employed for ultrasound guidance in accessing a patient's vasculature, TLS guidance during catheter advancement through the vasculature, and (as in later embodiments) ECG-based confirmation of catheter distal tip placement with respect to a node of the patient's heart. In one embodiment, the display 230 is an LCD device.

The probe 240 is employed in connection with the first modality mentioned above, i.e., ultrasound ("US")-based visualization of a vessel, such as a vein, in preparation for insertion of the catheter 10 into the vasculature. Such visualization gives real time ultrasound guidance for introducing the catheter 10 into the vasculature of the patient 60 and assists in reducing complications typically associated with such introduction, including inadvertent arterial puncture, hematoma, pneumothorax, etc.

As such, in one embodiment a clinician employs the first, US, modality to determine a suitable insertion site and establish vascular access, such as with a needle and introducer, then with the catheter. The clinician can then seamlessly switch, via button pushes on the probe button pad, to the second, TLS, modality without having to reach out of the sterile field. The TLS mode can then be used to assist in advancement of the catheter 10 through the vasculature toward the desired location.

FIG. 1 shows that the probe 240 further includes button and memory controller 242 for governing button and probe operation. The button and memory controller 242 can include non-volatile memory, such as EEPROM, in one embodiment. The button and memory controller 242 is in operable communication with a probe interface 244 of the console 220, which includes a piezo input/output component 244A for interfacing with the probe piezoelectric array and a button and memory input/output component 244B for interfacing with the button and memory controller 242.

Note that while a vein is typically depicted on the display 230 during use of the system 210 in the US modality, other body lumens or portions can be imaged in other embodiments. Note that the US mode can be simultaneously depicted on the display 230 with other modes, such as the TLS mode or ECG mode, if desired. In addition to the visual display 230, aural information, such as beeps, tones, etc., or vibratory/motion-based cues can also be employed by the system 210 to assist the clinician during catheter placement. Moreover, the buttons included on the probe 240 and the console button interface 232 can be configured in a variety of ways, including the use of user input controls in addition to buttons, such as slide switches, toggle switches, electronic or touch-sensitive pads, etc. Additionally, US, TLS, and ECG activities can occur simultaneously or exclusively during use of the system 210.

As just described, the handheld ultrasound probe 240 is employed as part of the integrated catheter placement system 210 to enable US visualization of the peripheral vasculature of a patient in preparation for transcutaneous introduction of the catheter. In the present example embodiment, however, the probe 240 is also employed to control functionality of the TLS portion, or second modality, of the system 210 when navigating the catheter toward its desired destination within the vasculature as described below. Again, as the probe 240 is used within the sterile field of the patient, this feature enables TLS functionality to be controlled entirely from within the sterile field. Thus the probe 240 is a dual-purpose device, enabling convenient control of both US and TLS functionality of the system 210 from the sterile field. In one embodiment, the probe can also be employed to control some or all ECG-related functionality, or third modality, of the catheter placement system 210, as described further below.

The catheter placement system 210 further includes the second modality mentioned above, i.e., the magnetically-based catheter TLS, or tip location system. The TLS enables the clinician to quickly locate and confirm the position and/or orientation of the catheter 10, such as a PICC, CVC, or other suitable catheter or medical device, during initial placement into and advancement through the vasculature of the patient 70. Specifically, the TLS modality detects a magnetic field generated by a magnetic element-equipped tip location stylet, which is pre-loaded in one embodiment into the longitudinally defined lumen 14 of the catheter tube 12, thus enabling the clinician to ascertain the general location and orientation of the catheter tip within the patient body. In one embodiment, the magnetic assembly can be tracked using the teachings of one or more of the following U.S. Pat. Nos. 5,775,322; 5,879,297; 6,129,668; 6,216,028; and 6,263,230. The contents of the afore-mentioned U.S. patents are incorporated herein by reference in their entireties. The TLS also displays the direction in which the catheter tip is pointing, thus further assisting accurate catheter placement. The TLS further assists the clinician in determining when a malposition of the catheter tip has occurred, such as in the case where the tip has deviated from a desired venous path into another vein.

As mentioned, the TLS utilizes a stylet to enable the distal end 12B of the catheter tube 12 to be tracked during its advancement through the vasculature. In one embodiment, the stylet includes a proximal end and a distal end, with a handle included at the proximal end and a core wire extending distally therefrom. A magnetic assembly is disposed distally of the core wire. The magnetic assembly includes one or more magnetic elements disposed adjacent one another proximate the stylet distal end and encapsulated by tubing. In the present embodiment, a plurality of magnetic elements is included, each element including a solid, cylindrically shaped ferromagnetic stacked end-to-end with the other magnetic elements. An adhesive tip can fill the distal tip of the tubing, distally to the magnetic elements.

Note that in other embodiments, the magnetic elements may vary from the design in not only shape, but also composition, number, size, magnetic type, and position in the stylet distal segment. For example, in one embodiment, the plurality of ferromagnetic magnetic elements is replaced with an electromagnetic assembly, such as an electromagnetic coil, which produces a magnetic field for detection by the sensor. Another example of an assembly usable here can be found in U.S. Pat. No. 5,099,845, entitled "Medical Instrument Location Means," which is incorporated herein by reference in its entirety. Yet other examples of stylets including magnetic elements that can be employed with the TLS modality can be found in U.S. Pat. No. 8,784,336, entitled "Stylet Apparatuses and Methods of Manufacture," which is incorporated herein by reference in its entirety. These and other variations are therefore contemplated by embodiments of the present invention. It should be appreciated herein that "stylet" as used herein can include any one of a variety of devices configured for removable placement within a lumen of the catheter to assist in placing a distal end of the catheter in a desired location within the patient's vasculature. In one embodiment, the stylet includes a guidewire.

FIG. 8 shows disposal of a stylet 330 substantially within the lumen in the catheter tube 12 such that the proximal portion thereof extends proximally from the catheter lumen, through the hub 16 and out through a selected one of the extension legs 18. So disposed within a lumen of the catheter, the distal end of the stylet 330 in the present embodiment is substantially co-terminal with the distal catheter end 12B such that detection by the TLS of the stylet distal end correspondingly indicates the location of the catheter distal end. In other embodiments, other positional relationships between the distal ends of the stylet and catheter or medical device are possible.

The TLS sensor 250 is employed by the system 210 during TLS operation to detect the magnetic field produced by the magnetic elements of the stylet 330. As seen in FIG. 8, the TLS sensor 250 is placed on the chest of the patient during catheter insertion. The TLS sensor 250 is positioned on the chest of the patient in a predetermined location, such as through the use of external body landmarks, to enable the magnetic field of the stylet magnetic elements, disposed in the catheter 10 as described above, to be detected during catheter transit through the patient vasculature. Again, as the magnetic elements of the stylet magnetic assembly are co-terminal with the distal end 12B of the catheter tube 12 in one embodiment (FIG. 8), detection by the TLS sensor 250 of the magnetic field of the magnetic elements provides information to the clinician as to the position and orientation of the catheter distal end during its transit.

In greater detail, the TLS sensor 250 is operably connected to the console 220 of the system 210 via one or more of the ports 252, as shown in FIG. 7. Note that other connection schemes between the TLS sensor and the system console can also be used without limitation. As just described, the magnetic elements are employed in the stylet 330 to enable the position of the catheter tube distal end 12B (FIG. 8) to be observable relative to the TLS sensor 250 placed on the patient's chest. Detection by the TLS sensor 250 of the stylet magnetic elements is graphically displayed on the display 230 of the console 220 during TLS mode. In this way, a clinician placing the catheter is able to generally determine the location of the catheter tube distal end 12B within the patient vasculature relative to the TLS sensor 250 and detect when catheter malposition, such as advancement of the catheter along an undesired vein, is occurring.

As discussed above, the system 210 includes additional functionality in the present embodiment wherein determination of the proximity of the catheter tube distal tip 12B relative to the SA or other electrical impulse-emitting node of the heart of the patient 60 can be determined, thus providing enhanced ability to accurately place the catheter distal tip in a desired location proximate the node. Also referred to herein as "ECG" or "ECG-based tip confirmation," this third modality of the system 210 enables detection of ECG signals from the SA node in order to place the catheter distal tip in a desired location within the patient vasculature. Note that the US, TLS, and ECG modalities are seamlessly combined in the present system 210, but can be employed in concert or individually to assist in catheter placement. In one embodiment, it is understood that the ECG modality as described herein can be included in a stand-alone system without the inclusion of the US and TLS modalities. Thus, the environments in which the embodiments herein are described are understood as merely example environments and are not considered limiting of the present disclosure.

As described, the catheter stylet 230 is removably predisposed within the lumen of the catheter tube 12 being inserted into the patient 60 via the insertion site 32. The stylet 330, in addition to including a magnetic assembly for the magnetically-based TLS modality, includes a sensing component, i.e., an internal, intravascular ECG sensor assembly, proximate its distal end and including a portion that is co-terminal with the distal end of the catheter tip for intravascularly sensing ECG signals produced by the SA node, in the present embodiment when the catheter 10 and accompanying stylet 330 are disposed within the patient vasculature. The intravascular ECG sensor assembly is also referred to herein as an internal or intravascular ECG sensor component.

The stylet 330 includes a tether 334 extending from its proximal end that operably connects to the TLS sensor 250, though other connection schemes to the system 210 are contemplated. As will be described in further detail, the stylet tether 334 permits ECG signals detected by the ECG sensor assembly included on a distal portion of the stylet 330 to be conveyed to the TLS sensor 250 during confirmation of the catheter tip location as part of the ECG signal-based tip confirmation modality.

External reference and ground ECG electrodes 336 attach to the body of the patient 60 in the present embodiment and are operably attached to the TLS sensor 250 to provide an external reference, or baseline, ECG signal to the system 210 and to enable the system to filter out high level electrical activity unrelated to the electrical activity of the SA node of the heart, thus enabling the ECG-based tip confirmation functionality. As shown, in the present embodiment, one external electrode 336 is placed on the patient skin proximate the upper right shoulder ("right arm" placement) while another external electrode is placed proximate the lower left abdomen ("left leg" placement). This electrode arrangement provides a lead II configuration according to Einthoven's triangle of electrocardiography. Operable attachment of the external electrodes 336 with the sensor 250 enables the ECG signals detected by the external electrodes to be conveyed to the console 220 of the system 210 or to another suitable destination. As such, the external electrodes 336 serve as one example of an external ECG sensor component. Other external sensors for detecting the baseline (reference) ECG signal external to the patient body can also be employed in other embodiments. In addition, other electrode locations are also possible.

Together with the external baseline ECG signal received from the external ECG sensor component (i.e., the external ECG electrodes 336 placed on the patient's skin), an internal, intravascular ECG signal sensed by the internal ECG sensor component (i.e., the stylet ECG sensor assembly of the stylet 330), is received by the TLS sensor 250 positioned on the patient's chest (FIG. 8) or other designated component of the system 210. The TLS sensor 250 and/or console processor 222 can process the external and internal ECG signal data to produce one or more electrocardiogram traces, including a series of discrete ECG complexes, on the display 230, as will be described. In the case where the TLS sensor 250 processes the external and internal ECG signal data, a processor is included therein to perform the intended functionality. If the console 220 processes the ECG signal data, the processor 222, controller 224, or other processor can be utilized in the console to process the data.

Thus, as it is advanced through the patient vasculature, the catheter 10 equipped with the stylet 330 as described above can advance under the TLS sensor 250, which is positioned on the chest of the patient as shown in FIG. 8. This enables the TLS sensor 250 to detect the position of the magnetic assembly of the stylet 230 (described further above), which is substantially co-terminal with the distal tip 12B of the catheter tube 12 as located within the patient's vasculature. The detection by the TLS sensor 250 of the stylet magnetic assembly is depicted on the display 230 during ECG mode.

The display 230 can further depict during ECG mode one or more ECG electrocardiogram traces produced as a result of patient heart's electrical activity as detected by the external and internal ECG sensor components described above. In greater detail, the ECG electrical activity of the SA node, including the P-wave of the trace, is detected by the external and internal sensor components and forwarded to the TLS sensor 250 and console 220. The ECG electrical activity is then processed for depiction on the display 230, as will be described further below.

A clinician placing the catheter can then observe the ECG data, which assists in determining optimum placement of the distal end or tip 12B of the catheter tube 12, such as proximate the SA node, for instance. In one embodiment, the console 220 includes the electronic components, such as the processor 222 (FIG. 7), necessary to receive and process the signals detected by the external and internal sensor components. In another embodiment, the TLS sensor 250 can include the necessary electronic components processing the ECG signals.

As already discussed, the display 230 is used to display information to the clinician during the catheter placement procedure. The content of the display 230 changes according to which mode the catheter placement system is in: US, TLS, or ECG. Any of the three modes can be immediately called up to the display 230 by the clinician, and in some cases information from multiple modes, such as TLS and ECG, may be displayed simultaneously. In one embodiment, as before, the mode the system is in may be controlled by the control buttons included on the handheld probe 240, thus eliminating the need for the clinician to reach out of the sterile field (such as touching the button interface 232 of the console 220) to change modes. Thus, in the present embodiment the probe 240 is employed to also control some or all ECG-related functionality of the system 210. Note that the button interface 232 or other input configurations can also be used to control system functionality. Also, in addition to the visual display 230, aural information, such as beeps, tones, etc., can also be employed by the system to assist the clinician during catheter placement.

Note that further details regarding the system 210 can be found in U.S. Pat. No. 8,848,382, issued Sep. 30, 2014, and entitled "Apparatus and Display Methods Relating to Intravascular Placement of a Catheter," which is incorporated herein by reference in its entirety.

It is appreciated that, in one embodiment, the first and second conductive pathways 40 and 50 (FIG. 1) can be used for initial placement of the catheter 10 into the vasculature of the patient 60 in lieu of the external and internal ECG sensor components (e.g., the stylet 330 and the external electrodes 336) described above in connection with FIGS. 7 and 8. In such a case, the first and second conductive pathways 40 and 50 would operably connect with the catheter placement system 210 via the tether 82 in the configuration shown in FIG. 2, or the tether 92 in the configuration shown in FIG. 5, for instance. As has been discussed further above, the first and second conductive pathways 40 and 50 are also employed in reconfirming catheter tube distal end position at a time later than the time of initial catheter placement. Thus, these and other variations in the interconnection of the catheter 10 with the catheter placement system 210 are therefore contemplated.

Embodiments of the invention may be embodied in other specific forms without departing from the spirit of the present disclosure. The described embodiments are to be considered in all respects only as illustrative, not restrictive. The scope of the embodiments is, therefore, indicated by the appended claims rather than by the foregoing description. All changes that come within the meaning and range of equivalency of the claims are to be embraced within their scope.

What is claimed is:

1. A method for reconfirming an initial position of a distal end of a catheter tube positioned in a patient, the catheter tube part of a catheter assembly, the method comprising:
   detecting an intravascular ECG signal via an inner conductive pathway in a lumen of the catheter tube;
   detecting a reference ECG signal via an outer conductive pathway deposited on an outer surface of the catheter tube;
   determining a current position of the distal end of the catheter tube based on detection of the intravascular ECG signal and the reference ECG signal; and
   comparing the current position of the distal end of the catheter tube with the initial position of the distal end of the catheter tube.

2. The method according to claim 1, wherein detecting the intravascular ECG signal and the reference ECG signal produces a lead configuration according to Einthoven's triangle of electrocardiography.

3. The method according to claim 1, wherein the inner conductive pathway is defined by a conductive stylet configured for insertion into the lumen of the catheter tube.

4. The method according to claim 3, wherein the conductive stylet is configured to operably connect with a conductive solution disposed in the lumen of the catheter tube.

5. The method according to claim 1, wherein the catheter assembly further comprises:
   a catheter hub;
   an extension leg tube having a distal end coupled to a proximal end of the catheter hub, the extension leg tube including a lumen in fluid communication with the lumen of the catheter tube; and
   a connector coupled to a proximal end of the extension leg tube, wherein the outer conductive pathway is deposited on the catheter hub, the extension leg tube, and the connector.

6. The method according to claim 5, wherein the catheter hub is a bifurcation hub, wherein the catheter tube comprises a second lumen, a second extension leg tube in fluid communication with the second lumen, and a second connector, and wherein the outer conductive pathway is deposited on the second extension leg tube and the second connector.

7. The method according to claim 5, wherein the inner conductive pathway extends along the catheter hub, the extension leg tube, and the connector.

8. The method according to claim 1, wherein the outer conductive pathway includes a conductive ink.

9. The method according to claim 1, wherein the outer conductive pathway includes a metallic material.

10. The method according to claim 9, wherein the metallic material includes copper.

11. The method according to claim 1, wherein the inner conductive pathway is disposed on a surface of the lumen of the catheter tube.

12. The method according to claim 1, wherein the inner conductive pathway is disposed within a wall of the catheter tube.

13. The method according to claim 1, wherein the inner conductive pathway extends distally of a distal end of the outer conductive pathway.

14. The method according to claim 13, wherein the distal end of the outer conductive pathway is positioned in the patient in the initial position of the distal end of the catheter tube.

15. The method according to claim 1, further comprising a connector interface configured to operably connect the inner conductive pathway to a medical device external to the patient.

16. The method according to claim 15, wherein the medical device comprises an ECG monitoring device, and wherein the connector interface comprises an electrode configured for placement on a skin surface of the patient, the method further comprising detecting ECG signals of a heart of the patient via the inner conductive pathway and the electrode.

\* \* \* \* \*